United States Patent [19]

Sumino et al.

[11] Patent Number: 4,779,623
[45] Date of Patent: Oct. 25, 1988

[54] SYSTEM FOR MEASURING SOUND VELOCITY OF TISSUE IN AN OBJECT AND SIMULTANEOUSLY PROVIDING A REAL-TIME B-MODE IMAGE OF THE OBJECT

[75] Inventors: Yoichi Sumino; Kiyoshi Okazaki, both of Tochigi, Japan

[73] Assignee: Kabushiki Kaisha Toshiba, Kawasaki, Japan

[21] Appl. No.: 894,810

[22] Filed: Aug. 8, 1986

[30] Foreign Application Priority Data

Aug. 9, 1985 [JP] Japan .................................. 60-176116
Aug. 9, 1985 [JP] Japan .................................. 60-176117
Nov. 11, 1985 [JP] Japan .................................. 60-252191

[51] Int. Cl.$^4$ .............................................. A61B 10/00
[52] U.S. Cl. .................................. 128/660.04; 73/597
[58] Field of Search ................................ 128/660-663; 73/597-599

[56] References Cited

U.S. PATENT DOCUMENTS

| | | | |
|---|---|---|---|
| 4,318,413 | 3/1982 | Iinuma et al. | 128/660 |
| 4,566,459 | 1/1986 | Umemura et al. | 73/597 X |
| 4,653,505 | 3/1987 | Iinuma | 73/597 X |
| 4,680,966 | 7/1987 | Nicolas | 73/597 |

*Primary Examiner*—Francis J. Jaworski
*Attorney, Agent, or Firm*—Finnegan, Henderson, Farabow, Garrett and Dunner

[57] ABSTRACT

A system for both measuring the sound velocity of tissue in an object and simultaneously providing a real-time B-mode image of the object. The system alternately image scans the object and cross scans the object so that a B-mode image of the object can be displayed while the object is being cross scanned by intersecting beams. By measuring the propagation times and displaying both a B-mode image of the object along with an image representing the cross scan signals, the user can view and correct errors caused by the reflection of echos waves from undesired reflection points, such as blood vessels.

21 Claims, 4 Drawing Sheets

SYSTEM FOR MEASURING SOUND VELOCITY OF TISSUE IN AN OBJECT AND SIMULTANEOUSLY PROVIDING A REAL-TIME B-MODE IMAGE OF THE OBJECT

BACKGROUND OF THE INVENTION

1. Field of the Invention

This invention relates to a system for examining the tissue of an object to be investigated and is especially directed to in vivo measurement of the sound velocity of the tissue. Through such measurement, the user of the system and method can determine the nature of the tissue and often perform medical or scientific diagnosis.

2. Description of the Prior Systems

This invention is related to the United States patent applications Ser. No. 737,472 of Iinuma, filed on May 24, 1985 and now U.S. Pat. No. 4,653,505; Ser. No. 816,902 of Hirama et al, filed on Jan. 7, 1986, and Ser. No. 875,687 of Okazaki, filed on June 18, 1986, each of which is hereby incorporated by reference. Each of the above applications are commonly owned and the reference to them in this application is not an admission that all or any of the applications constitute prior art which can be applied against this application.

Iinuma discloses a basic system and method for examination of the tissue of an object using an intersecting ultrasonic transmitting beam and receiving beam directed from or toward a phased array of ultrasonic transducer elements. A first sub-array on the phased array directs ultrasonic pulses toward the tissue along the transmitting beam. A distinct second sub-array on the phased array and distant from the first sub-array receives echos of the ultrasonic pulses reflected or scattered by the tissue along the receiving beam. The transducer elements of the first and/or second sub-arrays are excited in different timings to steer one or both of the transmitting and receiving beams so that the transmitting and receiving beams intersect at a cross point in the tissue. The propagation time required for the ultrasonic pulses from the first sub-array to travel to the second sub-array through the cross point is measured. A problem of this system is that it is difficult to obtain the actual steered angle of the transmitting and/or receiving beams because the actual steered angle is a function of the ultrasonic velocity in the tissue. The ultrasonic velocity in the tissue, however, is unknown. In that system the propagation length is calculated from the distance between the first and second sub-arrays, the distance between the adjacent elements, and the delayed time between the activation of the adjacent elements to steer the beam, using known geometric principles and Snell's law. Through that system, the average ultrasonic velocity from the first sub-array to the second sub-array through the cross point is obtained from the propagation length and the measured propagation time.

However, organs like a liver are covered by a fat or muscle layer, in which the ultrasonic velocity varies. So it is difficult to obtain an accurate ultrasonic velocity without in some manner cancelling the deviation caused by the fat and/or muscle layer.

Hirama et al. discloses a system and method for obtaining an accurate ultrasonic velocity by cancelling the effect of the fat and/or muscle layer by using two or three different crossed beams. Two crossed beams are sufficient, in a case where the fat or muscle layer has a uniform thickness. The use of three beams is preferable when the fat or muscle layer has a non-uniform thickness.

Okazaki discloses a system or method for mapping the ultrasonic velocities at the different points in the tissue.

In those systems and methods, a B-mode image is first obtained and frozen on the monitor. After that, an operator adjusts the cross point or the beams on the frozen B-mode image of the monitor.

Although the above inventions represent improvements over the prior art systems and methods of measuring the sound velocity within an internal tissue, they do not overcome all problems in this important diagnostic field. A patient's body is moving while one attempts to measure the sound velocity of his inner tissue. As a result of this movement, a blood vessel or similar object is likely to intrude upon the propagation path of the ultrasonic beams. Such a blood vessel or object will reflect the ultrasonic pulse much stronger than the normal tissue, such as the liver itself, and will cause an error in determining the sound velocity.

SUMMARY OF THE INVENTION

The present invention overcomes the problems and disadvantages of the prior systems by providing a system which permits a user to obtain a sound velocity measurement that does not include a reflection error caused by a foreign object, such as a blood vessel, in the same propagation path.

One object of the present invention is to provide a system for measuring the sonnd velocity of an internal tissue of an object using an ultrasonic beam transmitted from an ultrasonic transducer array.

Another object of the present invention is to provide a system for measuring the sound velocity while also displaying a real time image of the object.

It is a further object of the present invention to provide a system for measuring the sound velocity of an internal tissue by measuring only echos returned around the crossed point where a transmitting and receiving beam intersect.

It is a further object of the present invention to provide a system for displaying an incident sound velocity as well as an average sound velocity which is the average of a plurality of incident sound velocities.

It is still a further object of the present invention to provide a system for producing a B-mode image of the object and simultaneously measuring the sound velocity of the tissue by focused ultrasonic beams intersecting at a crossed point.

Additional objects and advantages of the invention will be set forth in part in the description which follows, and in part will be obvious from the description, or may be learned by practice of the invention. The objects and advantages will be realized and obtained by means of the elements and combinations particularly pointed out in the appended claims.

To achieve the foregoing objects, and in accordance with the purpose of the invention, as embodied and broadly described herein, the present invention comprises a system for measuring the sound velocity of a tissue within an object to be investigated, the system comprising: an array of transducer elements spaced at predetermined intervals for transmitting pulses into the object and receiving echos of said pulses reflected from said object; image scanning means coupled with said array for periodically activating a first sub-array of aligned transducer elements to periodically direct a plurality of beams into the object and receive the reflections of the beams, the image scanning means progressively activating a different set of transducer elements to thereby shift the first sub-array along the array's length; cross scanning means coupled with at least a second sub-array of tranducer elements and a separate third sub-array of transducers separated from said second sub-array by a predetermined distance, for activating the second and third sub-array to create respectively a transmitting beam and a receiving beam which intersect at a point within the tissue; control means coupled with said image scanning means and cross scanning means for activating said image scanning means and said cross scanning means alternatively according to a predetermined schedule; image means coupled with said array for producing from the transmitted and received beams a real-time B-mode image representative of the object; time measuring means coupled with at least said second and third sub-array for measuring the propagation time taken for a particular pulse to travel along the intersecting beams and for thereby determining a propagation time for the intersecting beams; computing means coupled with said time measuring means for determining the sound velocity of the tissue from the propagation time; and display means coupled with said image means and said computing means for displaying a real-time B-mode image of the object and its sound velocity.

It is to be understood that both the foregoing general description and the following detailed description are exemplary and explanatory only and are not restrictive of the invention, as claimed.

The accompanying drawings, which are incorporated in and constitute a part of this specification, illustrate an embodiment of the invention and, together with the description, serve to explain the principles of the invention.

BRIEF DESCRIPTION OF THE DRAWINGS

FIG. 5 is an explanatory chart illustrating how to set a crossed beam marker according to the disclosed embodiment of the present invention.

DESCRIPTION OF THE PREFERRED EMBODIMENT

Reference will now be made in detail to the present preferred embodiment of the invention, examples of which are illustrated in the accompanying drawings. Wherever possible, the same reference numbers will be used throughout the drawings to refer to the same or like elements.

Figure 1:
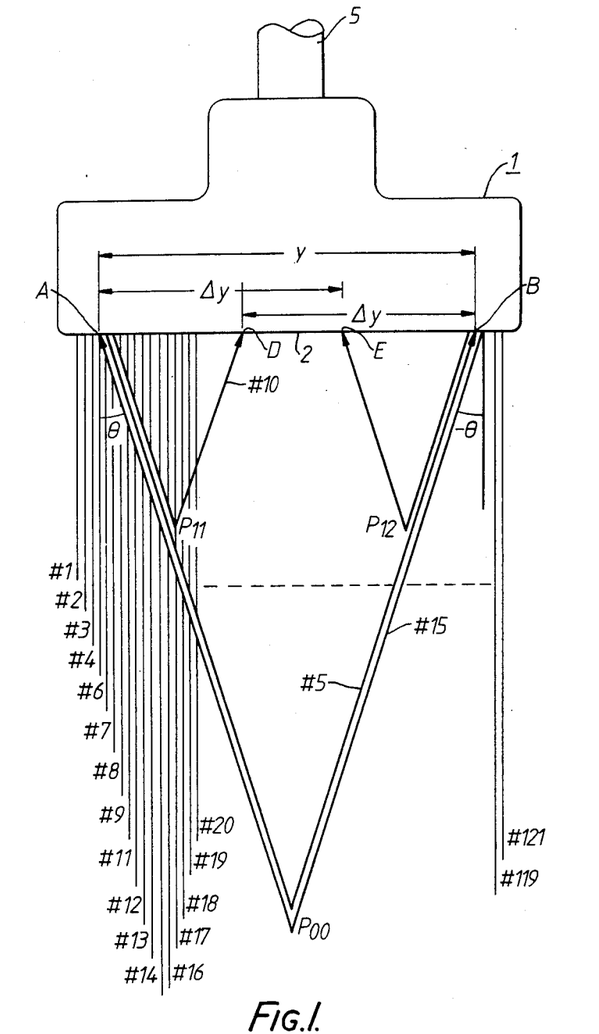
FIG. 1 is a schematic diagram showing an array of transducers of the present invention generally and illustrating the basic principles of the present invention.

FIG. 1 is explanatory of the basic principles applied by the present invention. In FIG. 1 an ultrasonic transducer 1 is connected to a transmitter and receiver (not shown) through a cable 5. The ultrasonic transducer 1 includes an array of ultrasonic transducer elements provided in its bottom surface 2. The transducer elements preferably are spaced from each other by the same predetermined distance. In use, the bottom surface 2 of transducer 1 is placed on a surface of an object to be investigated. The transducer 1 transmits ultrasonic pulses into the object and receives echos of the pulses that return from the object.

There are several ways to measure the sound velocity of the object according to conditions of tissue. They are described generally below.

In the basic method, a sub-array at a position A on the array transmits ultrasonic pulses toward a point $P_{00}$ along a transmitting beam steered at angle $\theta$. Another sub-array at a position B on the array which is located at distance Y from the position A receives echos reflected or scattered around the point $P_{00}$ along a receiving beam at the angle $-\theta$. A propagation time of the pulses from the sub-array at the position A to the sub-array at the position B through the point $P_{00}$ is measured. The length $L_0$ of path A-$P_{00}$-B is geometrically defined as follows:

$$L_0 = y/\sin\theta \tag{1}$$

where y is a distance between the positions A and B.

Usually, it is difficult to measure angle $\theta$ accurately, because C, the velocity of sound in the tissue, is unknown. But the transducer 1 is designed to transmit and receive these pulses at an angle $\theta_0$ into a medium, like a water, the sound velocity of which is well-known. Usually a wave is refracted when it travels from a certain medium into another medium having a different sound velocity. Therefore, the following relation is derived from Snell's law:

$$\sin\theta_O/C_O = \sin\theta/C \tag{2}$$

where $C_O$ and C are the sound velocities in water and the tissue, respectively. Therefore the sound velocity C of the tissue can be described as follows:

$$C = L_O/T \tag{3}$$

where T is the propagation time of the pulses from the sub-array at the position A to the sub-array at the position B.

The sound velocity C of the tissue is obtained from equations (1), (2) and (3) as follows:

$$C = \sqrt{C_0 y / T \sin\theta_0} \tag{4}$$

Thus, C can be obtained from known values $C_O$, Y, T and $\theta_O$ even if $\theta$ is unknown.

Furthermore a delayed time $\tau_o$ between adjacent elements to steer the beam is defined by the following equation:

$$\tau_o = (d/c_O) \sin\theta_O \tag{5}$$

where d is the distance between adjacent transducer elements. The equation (4) is rewitten as follows:

$$C = \sqrt{dy/T\tau_o} \tag{6}$$

Thus the sound velocity in the tissue on the path $A$-$P_{00}$-$B$ is obtained from the measurement of the propagation time.

In the second method, there is a fat and/or muscle layer near the surface which covers a liver. It is already known that sound velocity is slower (about 1400 m/sec) in a fat layer and faster (about 1600 m/sec) in a muscle layer than it is in the tissue like a liver. So it is difficult to determine the sound velocity of only liver because pulses go through such a fat or muscle layer.

In a case where a fat or muscle layer has a uniform thickness, it is possible to use a two beams to cancel the effect of the fat and/or muscle layer. In the second method, the sub-array at the position A tranmits another ultrasonic pulse toward a point $P_{11}$ along the transmitting beam. A sub-array at a position D between the positions A and B and located at distance $\Delta y$ from the position B receives echos of the ultrasonic pulses reflected or scattered at point $P_{11}$ along a receiving beam at the angle $-\theta$ to the bottom surface.

A second propagation time of the path $A$-$P_{11}$-$D$ is measured in addition to the first propagation time of the path $A$-$P_{00}$-$B$ obtained in the basic method. The difference $\Delta T$ in time between the first and second propagation times is representative of the propagation time of the path $P_{11}$-$P_{00}P_{12}$. The points $P_{11}$ and $P_{12}$ are symmetrically located relative to the point $P_{00}$. The path $P_{11}$-$D$ is as long as the path $P_{12}$-$B$, and it is assumed that the thickness of a fat or muscle layer into the object is the same between the positions A and B and does not extend beyond points $P_{11}$ and $P_{12}$. Therefore a propagation time propagating the paths $A$-$P_{11}$, $P_{11}$-$D$ and $P_{12}$-$B$ is cancelled by the first propagation time minus the second propagation time.

The length $\Delta L$ of the path $P_{11}$-$P_{00}P_{12}$ is defined as follows:

$$L = \frac{\Delta y}{\sin\theta} \qquad (7)$$

Therefore, the average sound velocity C of the path $P_{11}$-$P_{00}$-$P_{12}$ is described as follows from equations (2) and (5)

$$C = \sqrt{d\, \Delta y/\Delta T_{ro}} \qquad (8)$$

In the foregoing second method, it is assumed that a thickness of the fat or muscle layer is constant. This assumption is not always correct. In the third method, the sub-array at the position B transmits third pulses toward the point $P_{12}$ along the transmitting beam at the angle $-\theta$ to the bottom surface. A sub-array at a position E located at distance y from the position A receives echos of the third pulses reflected or scattered at the point $P_{12}$ along a receiving beam.

Thus, in the third method three different transmitting and receiving beams are used to measure the sound velocity and three kinds of the propagation times of the paths $A$-$P_{00}$-$B$, $A$-$P_{11}$-$D$ and $B$-$P_{12}$-$E$ are measured. The propagation times of paths $A$-$P_{11}$-$B$ and $B$-$P_{12}$-$E$ are averaged to minimize errors caused by different thicknesses of the fat or muscle layer between the positions A and B. From this averaged propagation time and the propagation time of the path $A$-$P_{00}$-$B$, the sound velocity for the path $P_{11}$-$P_{00}$-$P_{12}$ is obtained. In this way the errors caused by different thicknesses of the fat or muscle layer between the positions A and B is minimized.

In the fourth method the paths $A$-$P_{00}$-$B$, $A$-$P_{11}$-$D$ and $B$-$P_{12}$-$E$ are symmetrical to a central line passing through the position $P_{00}$ and bisecting the line AB, preferably perpendicular to line AB. In the fourth method measurements are performed symmetrically to the central line.

The sub-array at position B transmits a fourth pulse toward the point $P_{00}$. The sub-array at the position A receives echos of them reflected or scattered around point $P_{00}$. After the propagation times of the paths $A$-$P_{00}$-$B$ and $B$-$P_{00}$-$A$ and the propagation times of the paths $A$-$P_{11}$-$D$ and $B$-$P_{12}$-$E$ are averaged, the sound velocity for the path $P_{11}$-$P_{00}$-$P_{12}$ is obtained from the two averaged propagation times. Moreover, in a binary digital system, it is easier to control a system with 4 cycles, when compared with a system with 3 cycles.

The present invention can be applied to any of the above 4 methods and improves the precision of the measurement of sound velocity.

As an example, an application of the present invention to the fourth method will be explained. The explanation will also make it clear to those skilled in the art that the invention can be applied to other sound velocity measurement systems.

When measuring the sound velocity, the average sound velocity obtained in the fourth method from the four different pulses is measured again and again. These numerous measured values are then averaged to obtain a sound velocity measurement assumed to be the true value. Therefore, it takes a significant period of time to obtain an accurate value. During this time, a patient often is moving because of his breathing and other natural tendencies. Because of this movement, a strong reflector like a blood vessel often intrudes one or several of the paths being measured to obtain the sound velocity. The echos of the blood vessel produce sound velocity errors.

The system according to the present invention performs a real time B-mode scanning and a cross scanning for measurement of the sound velocity (cross beam scanning) simultaneously. For example, as shown in FIG. 1, four beams for the B-mode are successively scanned from the left edge of the array. Then, the propagation time of the path $A$-$P_{00}$-$B$ is measured. Next four beams for the B-mode scanning are successively scanned starting with the next to last transducer element to the left. That is, transducer elements 1-4 would be scanned the first time, transducer elements 2-5 the second time, and so forth. After four scans, the propagation time of the path $A$-$P_{11}$-$D$ is measured. This progression of B-mode scanning and cross beam scanning continues. Thus, in this example, cross beam scanning is performed once after every four B-mode scannings.

As an example, assume that the array has 128 elements and 32 elements are activated each time to obtain the B-mode scanning. While the scanning of 32 elements shifts from the left edge to the right edge, the object is image scanned 97 times, and the cross scanning and measurement for the sound velocity is performed 24 times. Therefore, when the fourth method is followed, six average sound velocities are obtained per one frame of B-mode.

In some systems, B-mode images have been obtained and frozen to allow a user to determine the locations of the points $P_{00}$, $P_{11}$ and $P_{12}$. In the present invention, however, the B-mode image obtained is a real time image which permits a user to monitor conditions existing at the time sound velocity is being measured.

Figure 2:
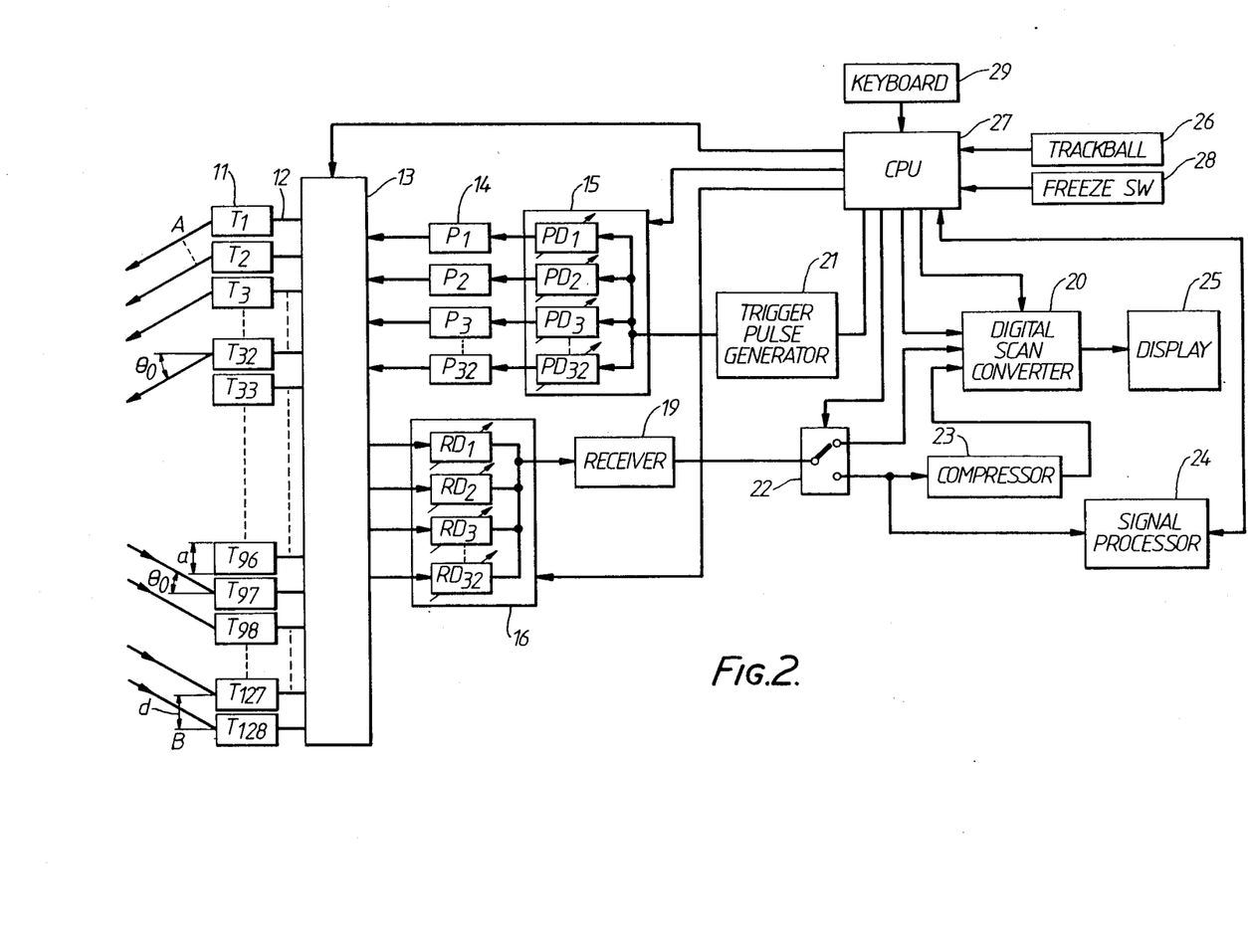
FIG. 2 is a block diagram illustrating an embodiment of an apparatus of the present invention.

A preferred embodiment of the present invention is shown in FIG. 2. In FIG. 2, an array of ultrasonic transducer elements 11 is arranged in the bottom surface 2 of the ultrasonic transducer 1. In the particular embodiment shown, the array 11 includes 128 transducer elements (T1 to T128). Each of the transducer elements is capable of transmitting an ultrasonic pulse when voltage is supplied to it and converting received echos of pulses into electrical signals. In the preferred embodiment, these elements (T1 to T128) have a width of 0.45 mm and are juxtaposed in a row at an interval d of 0.5 mm. The voltages supplied to some of the elements (T1 to T128) and electrical signals converted by them are transmitted and received, respectively, through cables 12 which are connected to them. A trigger pulse generator 21 generates 3.75 MHz trigger pulses responsive to 4 KHz rate pulses provided from a CPU 27. In the preferred embodiment, these trigger pulses are supplied to 32 transmitting delay lines 15. These delay lines 15 produce trigger pulses of delay times to steer the ultrasonic transmitting beam along a preselected steering angle. In the preferred embodiment, delay lines 15 can produce variable delay times to thereby change the steered angle as desired. Moreover, delay lines 15 can also provide the transducers wtth delay times that focus the transmitted beam electronically at a given target within the internal tissue to be investigated.

The delayed time $\tau(x)$ given to each transducer element is defined as follows:

$$\tau(x) = \left( \frac{F}{Co} [\sqrt{1 + (X/F)^2 + 2(X/F)\sin\theta_0} - 1] \right) \quad (9)$$

where x is a distance between the transducer element to be excited and the center of the beam on the array and F is a focal distance from the array. In the cross beam scanning, F is set to the respective points $P_{00}$, $P_{11}$ or $P_{12}$ to obtain strong echos around these points.

While B-mode scanning, the delayed time is as follows:

$$(x) = (F/Co)(\sqrt{1 + (X/F)^2} - 1) \quad (10)$$

When the beams are not focused, the delayed time as described in the equation (5) is given between each adjacent elements. The delayed time is provided by the CPU 27.

In the preferred embodiment, the trigger pulses are supplied to 32 pulsers 14. The pulsers 14 generate high voltage pulses to excite the transducer elements. Outputs of these pulsers 14 are supplied to multiplexer 13. The multiplexer selects, for example, the elements T1 to T32 at the position A or the elements T97 to T128 at the position B and connects the pulsers to them in the cross beam scanning. In the B-mode scanning the multiplexer 13 selects 32 successive elements and shifts them by one element at the rate pulses.

The 32 elements connected to the pulsers 14 by the multiplexer 13 are excited with the delayed high voltage pulses and produce the ultrasonic pulses along a steered and focused or a non-steered and focused transmitting beam. The array 11 contacts with the surface of the object to be investigated through a coating material (not shown), and the desired ultrasonic pulses and resultant steered and focused or non-steered and focused beam generated by the elements are transmitted into the object.

It is preferable to scan an object with fewer elements in a shallow region to provide a beam with a narrow width. This result can be obtained by varying the instructions provided to the CPU.

After the ultrasonic pulses are sent toward the object, the multiplexer 13 in the cross beam scanning selects, for example, 32 elements T97 to T128 at the position B, elements T32 to T64 at the position D, elements T81 to T112 at the position E or elements T1 to T32 at the position A, and connects them to receiving delay lines 16. Echo signals received by the elements are delayed in the same manner as the transmitted pulses. By applying the delay time, the elements at each position receive echos in opposite direction to the transmission.

In the B-mode scanning, the multiplexer 13 selects the same elements as the preceding excited elements and connects them to the receiving delay lines 16. Echoes received by the elements are focused at the predetermined point to improve a lateral resolution of B-mode image.

The receiver 19 amplifies and detects the summed echo signals and provides the signals in digital form to a selector 22. In cross scanning, the selector 22 connects the receiver 19 to a compressor 23 and a signal processor 24. In the B-mode scanning, the selector 22 connects the receiver to a digital scan converter (DSC) 20.

The compressor 23 samples the digital signals to display the same in the small regions on the display 25. The sampled digital signals are converted into A-mode signals and provided to the DSC 20. The signal processor 24 averages the signals to smooth the same and detects a peak of them to determine a propagation time for them.

Figure 3:
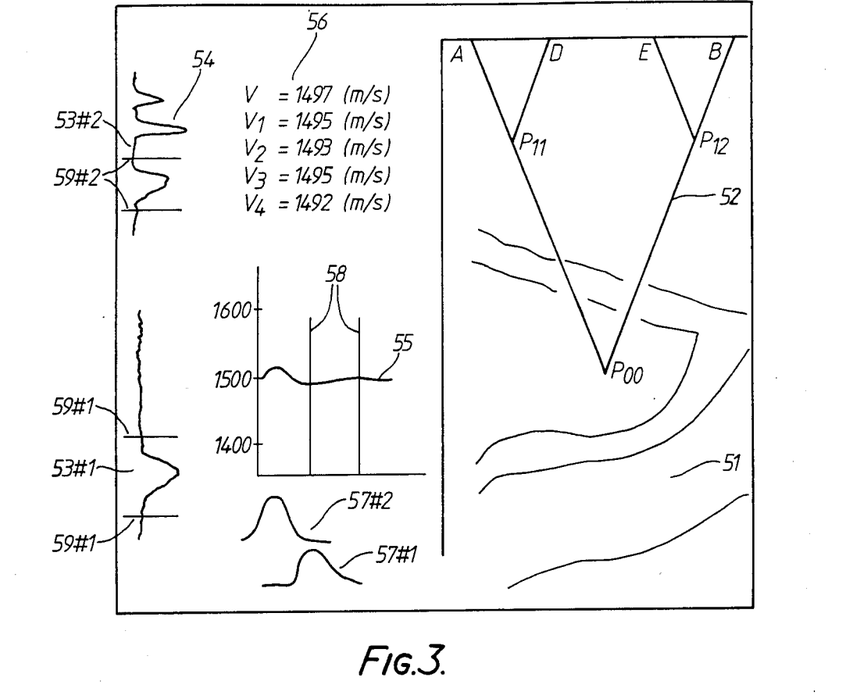
FIG. 3 is an explanatory chart illustrating an example of a display provided according to the disclosed embodiment of the present invention.

The DSC 20 is connected to a display 25, the format of which is as shown in FIG. 3. The DSC 20 includes a frame memory and a graphic memory (both not shown). The frame memory of the DSC 20 stores a B-mode image signal 51 from the receiver 19 and A-mode signals 53 #1 and #2 provided from the compressor 23. The A-mode signal 53 #1 is obtained from the path A-$P_{00}$-B and B-$P_{00}$-A. The A-mode signal 53 #2 is obtained from the path A-$P_{11}$-D and B-$P_{12}$-E. The DSC 20 refreshes both the A-mode signals every time the compressor 23 provides them.

The graphic memory of the DSC 20 is controlled by the CPU 27 and stores graphic patterns as shown in FIG. 3. One of them is a crossed beam marker 52 to indicate approximate paths for the cross beam scanning. Another marker 55 indicates a value averaging every four data of the sound velocities in analogue form. Bar markers 58 indicate a range to average the sound velocities of the marker 55 between them to select only good ones. Numerical numbers 56 represent this averaging value and the sound velocities for the four paths. Waveforms 57 #1 and #2 represent averaged wave forms of the echos of paths A-$P_{11}$-D or B-$P_{12}$-E and the echos of paths A-$P_{00}$-B or B-$P_{00}$-A.

Markers 59 #1 and #2 represent gates to eliminate echos except for the echos reflected from the cross points $P_{11}$, $P_{12}$, and $P_{00}$.

The DSC 20 overlays the data read from the frame memory and graphic memory in a television format and provides the overlayed data to the display 25. The display 25 displays the data from the DSC 20 as shown in FIG. 3.

A track ball 26 is connected to the CPU 27 to adjust the gate positions 59 #1 and #2 in FIG. 3. A freeze button 28 to cease both types of scanning is connected to the CPU 27. The key board 29 connected to the CPU 27 is for inputs of the data to set the scanning conditions like the points $P_{00}$, $P_{11}$ and $P_{12}$, the positions A, B, D and E of the sub-arrays, the focus depth of the B mode scanning and so on.

Figure 4:
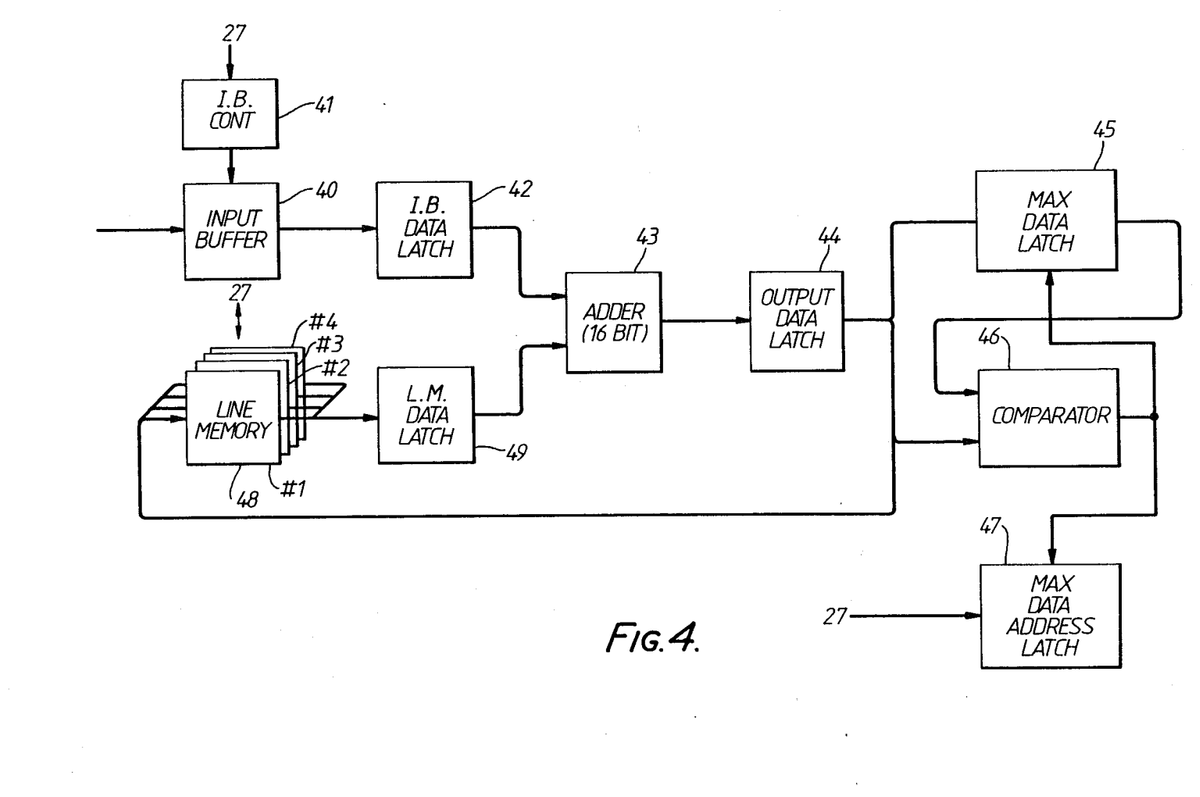
FIG. 4 is a block diagram illustrating the signal process of the disclosed embodiment of the present invention.

FIG. 4 illustrates a block diagram of the signal processor 24. An input buffer 40 receives digital signals from the receiver 19 through the selector 22. An input buffer controller (I.B. CONT) 41 counts addresses of the signals provided to the input buffer 40 and chooses the signals within the gate. The CPU 27 gives a start address and data length for the gate to the I.B. CONT 41.

Input buffer data latch 42 (I.B. DATA LATCH) temporarily stores the signals chosen by the input buffer 40 and the I.B. CONT 41 and provides it to an adder 43. The adder 43 adds an old signal stored in line memories 48 and the signal from the I.B. DATA LATCH 42 and provides the added signal to an output data latch 44. The output data latch 44 temporarily stores the added signal and provides it to the line memory 48, a max data latch 45, and a comparator 46. The line memories 48 #1, ... #4 are provided according to the fourth paths. Line memory 48 stores the added signals from the output data latch 44 and supplies them to the adder 43 through the line memory data latch 49 (L.M. DATA LATCH). When the line memory stores 99 time-added signals, the comparator compares the maximum signal stored in the maximum data latch 45 with the signals from the output data latch 44. If the data in output data latch 44 is greater than the existing data in maximum data latch 45, the max data latch 45 replaces the old stored data with the new data. The max data address latch 47 stores the address of the data provided from the comparator 46.

In this way, a peak address of the echo signals is detected. The CPU 27 accesses the max data address latch 47, reads the peak address and calculates a propagation time from it. After that, line memories 48 are refreshed.

CPU 27 also selectively accesses the line memories 48 when the freeze button 28 is pushed and writes the signals in the graphic memory of the DSC 20 to display the waves 57 #1 and #2 in FIG. 3.

Now an operation of the preferred embodiment will be explained referring to FIGS. 1 to 3.

In this example, the cross beam scanning for the measurement of sound velocity is performed every 5th rate pulse. Propagation times of the paths A-$P_{00}$-B, A-$P_{11}$-D, B-$P_{00}$-A and B-$P_{12}$-E are measured in turn by beams at rate pulses #5, #10, #15, #20, ..., #120 as shown in FIG. 1.

At the other rate pulses, the B-mode scanning for real-time imaging of the object is performed. The beams #1, #2, #3, #4, #6, ..., #121 are parallel scanned by shifting 32 elements by one element.

The echo signals obtained by the cross beam scanning are thinned by the compressor 23 and written in the frame memory of the DSC 20 as A-mode signals 53 #1 and #2. Also, they are provided to the signal processor 24. A hundred of the echo signals obtained by the cross beam scanning for four paths are averaged and smoothed by the signal processor 24 because incidental echo signals have speckle noises. Every time that 100 of the echo signals for four paths are averaged and smoothed, the four peaks of the averaged and smoothed echo signals for the four paths are detected by the signal processor 24. The CPU 27 reads the four addresses for the four peaks in the echo signals to translate them into the propagation times for the four paths. These propagation times are converted into sound velocities for four paths according to the following equations:

$$V1 \text{ or } V3 = \sqrt{dy/T_{1To}} \tag{11}$$

$$V2 \text{ or } V4 = \sqrt{d(y - \Delta y)/T_{2To}} \tag{12}$$

where V1, V2, V3 and V4 are respectively the sound velocities for the paths A-$P_{00}$-B, B-$P_{00}$-A, A-$P_{11}$-D and B-$P_{12}$-E, and T1 and T2 are respectively the propagation times for the paths A-$P_{00}$-B or B-$P_{00}$-A, and A-$P_{11}$-D and B-$P_{12}$-E. These velocities V1, V2, V3 and V4 are written in the graphic memory of the DSC 20 by the CPU 27 like the numerals 56 in FIG. 3.

Further, the CPU 27 averages the propagation times for the paths A-$P_{00}$-B and B-$P_{00}$-A and those for the paths A-$P_{11}$-D and B-$P_{12}$-E. Then the CPU 27 calculates the sound velocity V cancelling the effect of fat and/or muscle layer in the abdominal wall according to the following equation:

$$V = d\sqrt{\Delta y/T'_{To}} \tag{13}$$

where T' is the difference time between the averaged propagation times. The CPU 27 averages this sound velocity and the last three sound velocities previously obtained thereby.

This averaged sound velocity is written in the graphic memory of the DSC 20 by the CPU 27 like the numeral 56 in FIG. 3. Also, the sound velocity is written in the graphic memory like the graphic curve 55 in FIG. 3. The CPU further calculates the average sound velocity averaging the sound velocities between the bar markers 58 on the curve 55. Thereby, good sound velocities are selected to obtain the desired average.

When a strong echo 54 issues from any point other than points $P_{00}$, $P_{11}$ and $P_{12}$, the echo 54 is detected and displayed as shown in FIG. 3. The gates 59 #1 and #2 can then be adjusted by the track ball 26 to obtain only the echo signals around these desired points $P_{00}$, $P_{11}$ and $P_{12}$. The echo signals between the gates 59 #1 and #2 are selected by the input buffer 40 and the I.B. CONT 41.

The echo signals obtained by the B-mode scanning are written at the locations in the frame memory of the DSC 20 corresponding to the locations from which the beams are scanned.

Both the B-mode scanning and cross beam scanning are performed by turns, as previously explained, until the freeze button 28 is pushed. Therefore a real time B-mode image 51, incidental A-mode signals 53 #1, #2, the newest sound velocities 56, and the changing curves 55 and 58 are displayed accompanying the markers 52, 59 #1 and #2 on the display 25.

When the freeze button is pushed, both scannings are stopped. The average signals stored in the line memories 48 are read and written in the graphic memory by the CPU. They are displayed like the waves 57 #1 and #2 in FIG. 3.

The positions A, B, C and D for the crossed beam scanning is variable in the preferred embodiment. When these positions are determined, the CPU 27 writes a plurality of dots 60 in the graphic memory of the DSC 20 to display the dots 60 on the display 25 as shown in FIG. 5.

First, the point $P_{00}$ is determined by the track ball 26. Since the steered angles of a transmitting and receiving beams are fixed, the positions A and B are determined on the array. Second the depth of the points $P_{11}$ and $P_{12}$ is determined by the track ball 26. Thereby the positions D and E are determined on the array. The CPU 27 activates sub-arrays of these positions.

Although the above system is capable of providing sound velocities from one reading, it is preferable to average the sound velocities, as disclosed above.

It will be apparent to those skilled in the art that various modifications and variations can be made in the practice of the present invention without departing from the scope or spirit of the invention. By means of example only, the present invention can determine sound velocity and average sound velocity by any of the four methods disclosed in this application, as well as by other methods of determining sound velocity. It is intended that the specification and examples be considered as exemplary only, with the true scope and spirit of the invention being defined by the following claims.

What is claimed is:

1. A system for measuring the sound transmission velocity within a tissue in an object to be investigated, the system comprising:
    an array of transducer elements spaced at predetermined intervals for transmitting pulses into the object and receiving echos of said pulses reflected from said object, said array including at least three sub-arrays of transducer elements: a shifting first sub-array for sequentially image scanning the object and a second and a third sub-array, being separated at predetermined distances from one another, for cross scanning the object;
    image scanning means coupled with said array for periodically activating said first sub-array of aligned transducer elements to periodically direct a plurality of beams into the object and receive the reflections of the beams, the image scanning means progressively activating a different set of transducer elements to thereby shift the first sub-array along the array's length;
    cross scanning means, coupled with said second sub-array and said third sub-array, for activating the second and third sub-array to create respectively a transmitting beam and a receiving beam which intersect at a point within the tissue;
    scanning control means coupled with said image scanning means and said cross scanning means for activating said image scanning means and said cross scanning means alternatively for a plurality of times according to a predetermined schedule in which said image scanning means scans along the array a predetermined plurality of N times before the image scanning means is temporarily deactivated and the cross-scanning means is activated;
    image means coupled with said array for producing from the sequentially transmitted and received beams from the first array of real-time B-mode image signal representative of the object;
    time measuring means coupled with at least said second and third sub-array for measuring the propagation time taken for the respective pulses to travel along the intersecting beams and for thereby determining propagation times for the intersecting beams;
    computing means coupled with said time measuring means for determining the sound transmission velocity within the tissue from the propagation times; and
    display means coupled with said image means and said computing means for simultaneously displaying a real-time B-mode image of the object and its sound transmission velocity.

2. The system according to claim 1 wherein said image scanning means on each activation from said control means excites the same transducer elements in the first sub-array to both transmit and receive ultrasonic echos and wherein said control means activates the image scanning means to scan along the array for a predetermined plurality of times before the control means deactivates the image scanning means and activates the cross sector scanning means.

3. The system according to claim 2 wherein said second scanning means scans the object with the intersecting beams of four paths $A-P_{00}-B$, $A-P_{11}-D$, $B-P_{00}-A$ and $B-P_{12}-E$.

4. The system according to claim 2 wherein said time measuring means includes:
    gating means for gating the echo signals provided from said second scanning means between preset addresses;
    summing means for summing the echo signals from said gating means for said paths respectively to smooth the echo signals; and
    peak detecting means for detecting the summed echo signals for said paths to determine the propagation times for said paths.

5. The system according to claim 1 further comprising means for producing and displaying an image representative of the position and direction of the intersecting beams.

6. The system according to claim 5 further comprising a means for producing and displaying A-mode images of signals of the intersecting beams.

7. The system according to claim 6 further comprising gate means to eliminate echos reflected from locations in the tissue other than the point of intersection.

8. The system according to claim 7 further comprising merans to adjust the width of the gate means.

9. The system according to claim 8 further comprising means to focus the depth of the image scanning means.

10. The system according to claim 7 wherein said system further includes means for generating markers indicative of said preset address on the A-mode signals, and means for adjusting said markers.

11. The system according to claim 6 wherein said display means further displays the echo signals provided from said second scanning means as A-mode signals.

12. The system according to claim 6 wherein said display means further displays the summed echo signal provided from the summing means.

13. The system according to claim 6 wherein said display means further displays a changing curve of the sound velocity.

14. The system according to claim 1 wherein said cross-scanning means includes beam steering means coupled with said second and third sub-array for exciting at least one of the second and third sub-arrays at a predetermined time delays.

15. A system for measuring the sound transmission velocity within a tissue in an object to be investigated, the system comprising;
   an array of transducer elements spaced at predetermined intervals for transmitting ultrasonic pulses into the object and receiving echos of said pulses reflected from said object, said array including at least five sub-arrays: a shifting first sub-array for sequentially iamge scanning the object, two sub-arrays being located at positions A and B respectively that are separated at a predetermined distance form one another, and two other sub-arrays being symmetrically located at predetermined positions D and E located between positions A and B, said second through fifth sub-arrays being adapted for cross scanning the object;
   a first scanning means coupled with said first sub-array for activating the first sub-array to transmit and receive parallel beams from common transducer elements and for sequentially activating a different first array of transducer elements to thereby sequentially shift the transmitting and receiving beams along the array;
   a second scanning means for causing said other four sub-arrays to scan the object with at least three pairs of transmitting and receiving beams that intersect at different points $P_{00}$, $P_{11}$ and $P_{12}$, one of said transmitting and receiving beams of each interesting pair being steered at an angle $\theta$ and the other being steered at an angle $-\theta$;
   scanning control means, coupled with said first and second scanning means, for alternatively activating said first and second scanning means for a plurality of times according to a predetermined schedule in which said image scanning means scans along the array a predetermined plurality of N times before the image scanning means is temporarily deactivated and the cross-scanning means is activated;
   time measuring means coupled with said second, third, fourth and fifth sub-arrays for measuring at least three propagation times taken for the respective pulses to travel along the intersecting transmitting and receiving beams and for thereby determining the propagation times for the three intersecting beams;
   image means coupled with said first sub-array for producing an image signal representative of the object;
   computing means coupled with said time measuring means for determining the sound velocity of the tissue from the propagation times; and
   displaying means coupled with said image means and said computing means for displaying an image of the object and its sound transmission velocity.

16. A system for measuring the sound transmisison velocity within a tissue in an object to be investigated, the system comprising:
   an array of transducer elements spaced at predetermined intervals for transmitting pulses into the object and receiving echos of said pulses reflected from said object, said array including at least three sub-arrays of transducer elements: a shifting first sub-array for sequentially image scanning the object and a second and a third sub-array, being separated at predetermined distances from one another, for cross-scanning the object;
   image scanning means coupled with said array for periodically activating said first sub-array of aligned transducer elements to periodically direct a plurality of beams into the object and receive the reflections of the beams, the image scanning means progressively activating a different set of transducer elements to thereby shift the first sub-array along the array's length;
   cross-scanning means, coupled with said second sub-array and said third sub-array, for activating the second and third sub-array to create respectively a transmitting beam and a receiving beam which intersect at a point within the tissue;
   selector means coupled with said image scanning means and said cross-scanning means and having a first output and a second output;
   control means coupled with said image scanning means, said cross-scanning means, and said selector mens for activating said image scanning means and said cross-scanning means alternatively for a plurality of times according to a predetermined schedule in which said image scanning means scans along the array a predetermined plurality of N times and said selector means passes the received signals through the first output that same plurality of N times before the image scanning means and the first output of said selector means is temporarily deactivated and the cross scanning means and the second output of said selector means is activated;
   image processing means coupled with the first output of said selector means for producing from the sequentially transmitted and received beams from the first array a real-time B-mode image signal representative of the object;
   signal processing means coupled with the second output of said selector means for averaging the echo signals obtained from the cross beam scanning means and detecting the peaks of the echo signals;
   computing means coupled with said signal processor means for measuring the propagation time taken for a particular pulse to travel along the intercepting beams and for determining the sound transmission velocity within the tissue from the measured propagation time; and
   display means coupled with said image means and said computing means for display a real time B-mode image of the object and its sound transmission velocity.

17. The system according to claim 16 further comprising a compressor means coupled with the second output of said selector means for sampling signals representative of the signals received by the cross-scanning means and providing to the display means an A-mode signal representative of the sample signal.

18. The system according to claim 16 wherein said display means includes both a frame memory for storing a B-mode image from the first output of said selector means and an A-mode image from the compressor means and a graphic memory for storing graphic patterns representative of the crossed beams and the value of the sound transmission velocity determined by said computing means.

19. The system according to claim 16 further comprising gates and gate adjusting means to obtain only the echo signals proximate to the desired intersection points of the transmitted and received cross-scanned beams.

20. A method for measuring the sound transmission velocity within a tissue in an object and simutlaneously providing an image of the object to be investigated, the method comprising the steps of:

placing against the object an array of transducer elements spaced at predetermined intervals for transmitting pulses into the object and receiving echos of said pulses reflected from said object, said array including at least three sub-arrays of transducer elements: a shifting first sub-array for sequentially image scanning the object and a second and a third sub-array, being separated at predetermined distances from one another, for cross-scanning the object;

image scanning the object by progressively activating N different sets of transducer elements along the array's length to shift the first sub-array and to direct from each set of a plurality of beams into the object and receive the reflections of the beams to obtain image scanning data;

after N different sets of transducer elements have been activated to image scan the object N times, cross-scanning the object by activating the second array to create a transmitting beam and activating the third sub-array to create a receiving beam, the transmitting and receiving beams intersecting at a point within the tissue;

alternatively image scanning and cross beam scanning the object a plurality of times according to the above sequence;

combining the obtained image scanning data to produce a real-time image of the object;

measuring the propagation times for the respective cross scanned beams to travel along each set of intersecting beams and determining the respective sound transmission velocity within the tissue from the measured propagation times;

averaging the plurality of determined transmission sound velocities to obtain an average value; and after alternatively image scanning and cross scanning the object a plurality of times, simultaneously displaying a real-time B-mode image of the object and the average sound transmission velocities of the tissue in the object.

21. The method of claim 20 further comprising the steps of displaying a graphic representation of the position and angles of the cross scanned beams.

* * * * *